United States Patent
Chen et al.

(10) Patent No.: US 8,398,545 B2
(45) Date of Patent: Mar. 19, 2013

(54) LARYNGOSCOPE WITH A MOVABLE IMAGE-CAPTURING UNIT

(75) Inventors: Tien-Sheng Chen, Taipei (TW);
Hui-Bih Yuan, Taipei (TW)

(73) Assignee: Tien-Sheng Chen, Taipei (TW)

( * ) Notice: Subject to any disclaimer, the term of this patent is extended or adjusted under 35 U.S.C. 154(b) by 1031 days.

(21) Appl. No.: 11/776,760

(22) Filed: Jul. 12, 2007

(65) Prior Publication Data

US 2008/0177148 A1    Jul. 24, 2008

(30) Foreign Application Priority Data

Jan. 19, 2007   (TW) ............................... 96201170 U

(51) Int. Cl.
*A61B 1/267* (2006.01)
(52) U.S. Cl. ........................................ 600/188; 600/199
(58) Field of Classification Search ........... 600/185–200
See application file for complete search history.

(56) References Cited

U.S. PATENT DOCUMENTS

| | | | | | |
|---|---|---|---|---|---|
| 3,884,222 | A | * | 5/1975 | Moore | 600/188 |
| 4,360,008 | A | * | 11/1982 | Corazzelli, Jr. | 600/194 |
| 5,095,888 | A | * | 3/1992 | Hawley | 600/194 |
| 5,551,946 | A | * | 9/1996 | Bullard | 600/194 |
| 6,135,948 | A | * | 10/2000 | Lee | 600/189 |
| 6,840,903 | B2 | * | 1/2005 | Mazzei et al. | 600/188 |
| 6,890,298 | B2 | * | 5/2005 | Berci et al. | 600/185 |
| 2002/0022769 | A1 | * | 2/2002 | Smith et al. | 600/188 |
| 2003/0195390 | A1 | * | 10/2003 | Graumann | 600/188 |
| 2007/0179342 | A1 | * | 8/2007 | Miller et al. | 600/188 |
| 2007/0197873 | A1 | * | 8/2007 | Birnkrant | 600/160 |
| 2008/0064926 | A1 | * | 3/2008 | Chen | 600/110 |

* cited by examiner

*Primary Examiner* — Kevin T Truong
*Assistant Examiner* — Larry E Waggle, Jr.
(74) *Attorney, Agent, or Firm* — Alan Kamrath; Kamrath IP Lawfirm, P.A.

(57) ABSTRACT

A laryngoscope a handgrip, a blade, and an image-capturing unit for capturing an image. The blade is connected to the handgrip, and the image-capturing unit is movably secured on the blade. In use, users may adjust the view of the laryngoscope by moving the image-capturing unit.

17 Claims, 8 Drawing Sheets

LARYNGOSCOPE WITH A MOVABLE IMAGE-CAPTURING UNIT

BACKGROUND OF THE INVENTION

1. Field of the Invention

The present invention relates to a laryngoscope. More particularly, the Present invention relates to a laryngoscope with a movable image-capturing unit.

2. Description of the Related Art

Endotracheal intubation is critical for maintaining the breathing function of a patient under general anaesthesia. In most cases, to prevent the occurrence of hypoxia, anaesthetists have to complete the intubation by inserting an endotracheal tube into a patient's trachea in a very short period of time to provide oxygen thereinto promptly. Therefore, it is extremely important for anaesthetists to perform the intubation efficiently.

To intubate quickly, most anaesthetists take advantage of a laryngoscope to observe the condition of a patient's upper airway. Please refer to FIG. 1. An early laryngoscope 10P mainly consists of a handgrip 20 and a blade 30. It is generally used on a patient lying face up with the mouth open. The anaesthetists may press the tongue base down with the blade 30 by holding the handgrip 20 to move away the epiglottis cartilage and to gain a clearer view of the trachea to complete the intubation procedure correctly. However, there is great variation among patients' anatomies, and there are many cases in which the early laryngoscope 10P cannot be used satisfactorily.

To overcome this shortcoming, different solutions have been provided by several improved laryngoscope designs. For example, some laryngoscopes have different pushing mechanisms installed on blades to improve the visual field, such as those disclosed in US2005/0234303A1. Some other laryngoscopes have a stationary image-capturing unit, as the element 40P shown in FIG. 1, in order to facilitate observation of the trachea. However, said improvements are still unable to fully address users' needs. First, the pushing mechanism used in the former improvement may inevitably hurt the upper airway of a patient. Concerning the latter improvement, the view of the image-capturing unit 40P, shown in FIG. 2, can become obstructed by the patient's tissues or organs, such as the epiglottis cartilage 100, or by the endotracheal tube, since the image-capturing unit 40P is fixed on the blade 30 with a fixed length and curvature. Therefore, this kind of improvement still fails to provide a viewing mechanism adjustable to different patients, and, in some cases, users are unable to observe the trachea during the intubation.

Thus, there is a need for a laryngoscope suitable for different anatomies to make intubation and the observation of the upper airways more convenient.

SUMMARY OF THE INVENTION

It is therefore an object of the present invention to provide a laryngoscope having a movable image-capturing unit which may enable users to observe the area around the trachea more clearly.

It is another object of the present invention to provide a laryngoscope having an adjustment piece by which users may be able to move the image-capturing unit.

It is still another object of the present invention to provide a laryngoscope capable of transmitting an image captured by the image-capturing unit to a display through either wired or wireless transmission.

To attain the foregoing objects, the laryngoscope of the present invention mainly comprises a handgrip; a blade connected to the handgrip; and an image-capturing unit secured on and may be moved on the blade.

The laryngoscope of this invention may further comprise an adjustment piece which comprises a pushing part and a supporting part, with said pushing part having a front end and a rear end, and with said supporting part having a fixed end connected to the handgrip and a joint end pivotally mounted to the rear end of the pushing part. Users may move the image-capturing unit on the blade by pushing or pulling the adjustment piece.

Furthermore, to increase the efficiency of the intubation, users may sleeve the endotracheal tube onto an image-capturing unit through a side aperture on the endotracheal tube, known as the Murphy eye. After locating the image-capturing unit to a desirable position, users may then push forward the endotracheal tube to complete the intubation.

In addition, the laryngoscope of this invention enables the wireless transmission of the image captured by the image-capturing unit through the installation of an emitter and a receiver. Since the technique of wireless transmission is already known in the art, further elaboration is omitted here. Self-evidently, the image of the present invention may also be transmitted by a wired transmission. Similarly, since the technique of wired transmission is already known in the art, further elaboration is also omitted.

To provide a more convenient observation, the laryngoscope of the present invention may also be equipped by a display to show the image captured by the image-capturing unit. It should be noted that the display may also be installed externally and receive the image signal from the image-capturing unit by wired or wireless transmission.

Other objects, advantages, and novel features of the invention will become more apparent from the following detailed description in conjunction with the accompanying drawings.

BRIEF DESCRIPTION OF THE DRAWINGS

These and other objects and advantages of the present invention will become apparent from the following description of the accompanying drawings, which disclose several embodiments of the present invention. It is to be understood that the drawings are given for the purpose of illustration only, and not as a definition of the invention.

Similar reference numerals are used to denote similar elements within the different figures.

DETAILED DESCRIPTION OF THE PREFERRED EMBODIMENT

To further clarify the features of the present invention, several preferred embodiments are disclosed hereafter.

Figure 1:
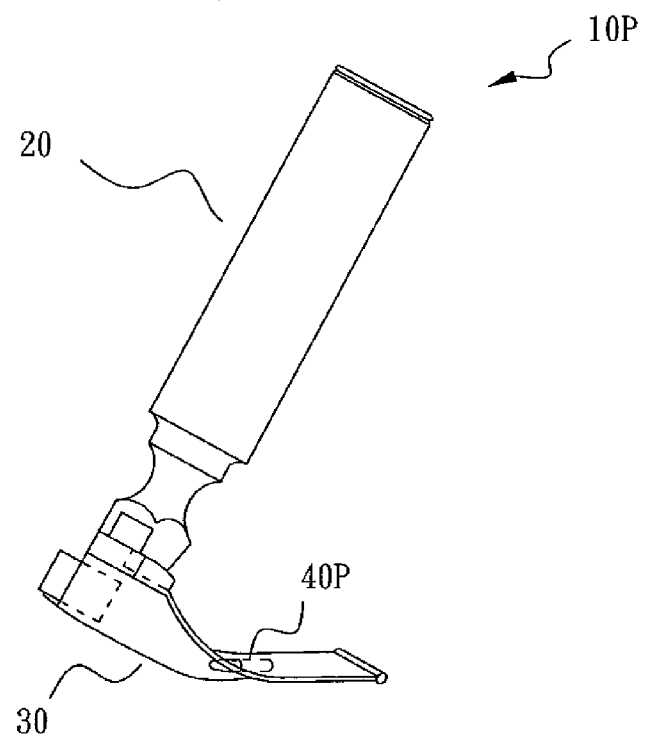
FIG. 1 is a three-dimensional diagram of a laryngoscope used in the prior art.
Figure 2:
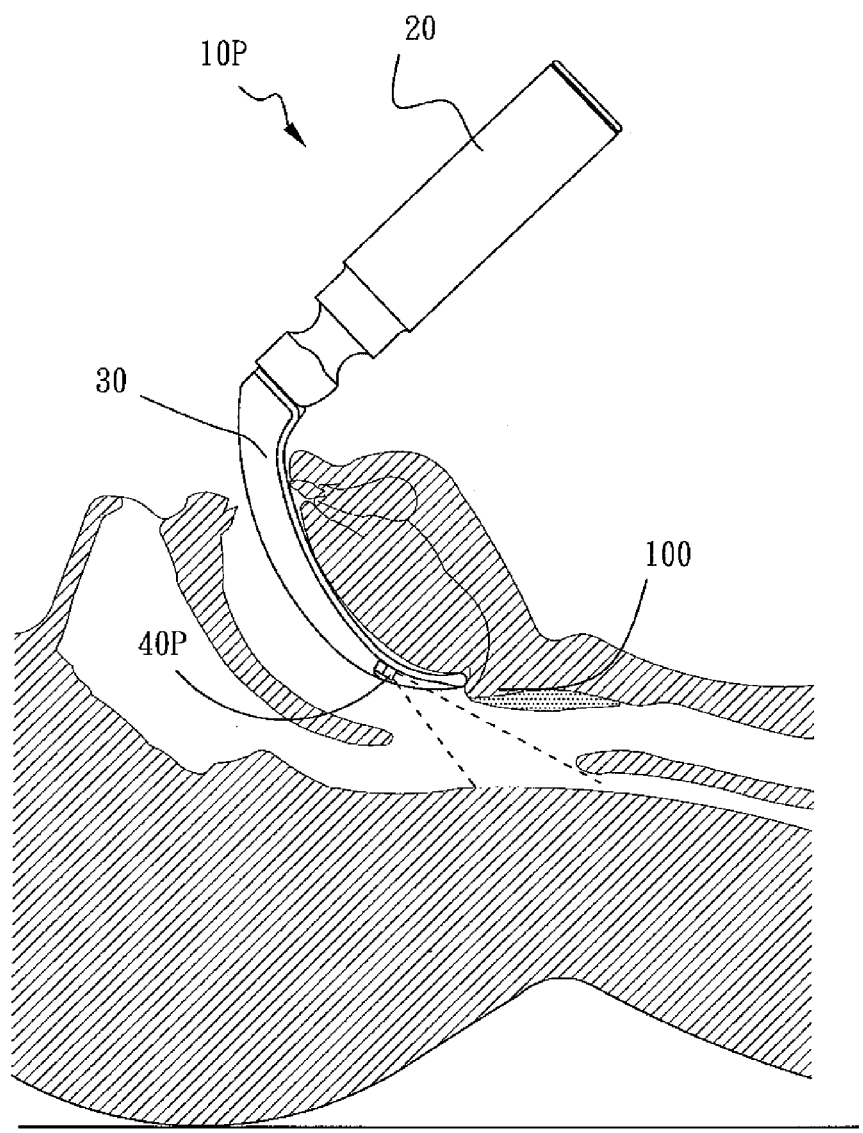
FIG. 2 illustrates the status in use of a laryngoscope used in the prior art.
Figure 3:
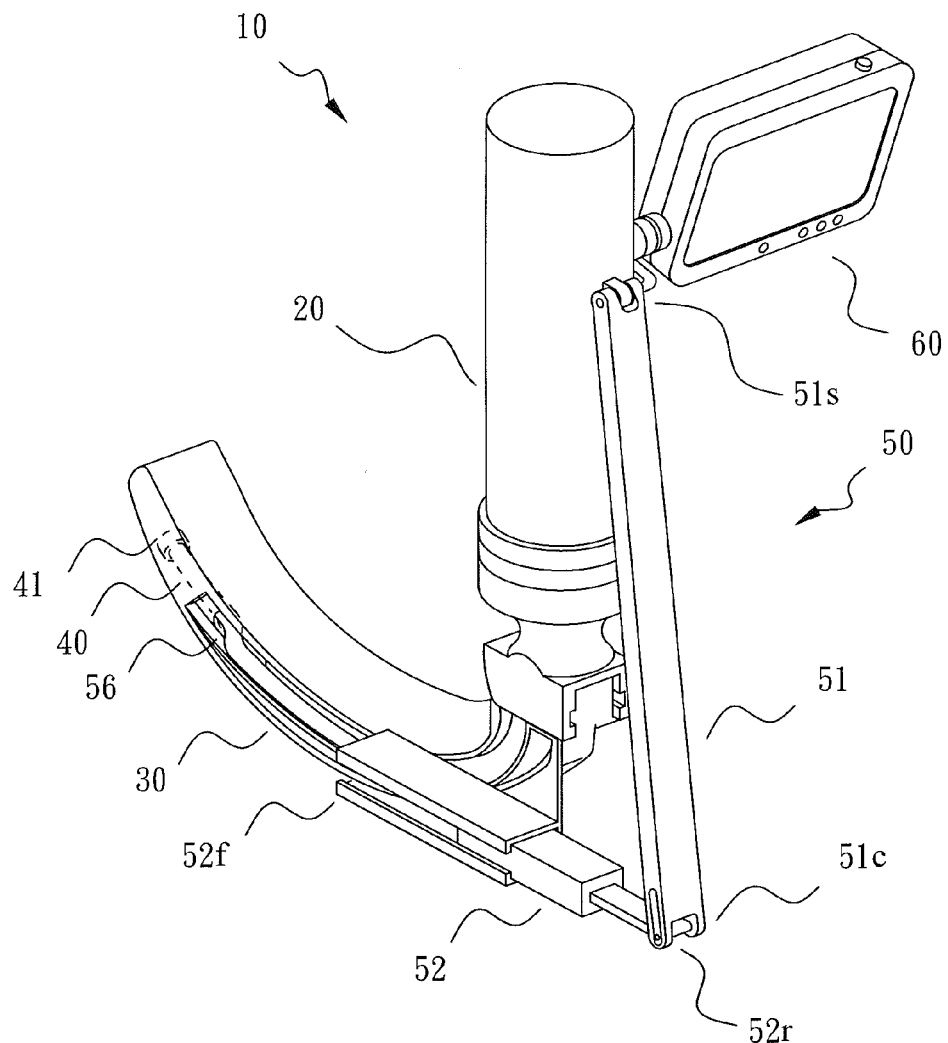
FIG. 3 is a three-dimensional diagram of a laryngoscope of the present invention.

Please refer to FIG. 3 for a three-dimensional diagram of a laryngoscope 10 of the present invention. As shown, the laryngoscope 10 mainly comprises a handgrip 20, a blade 30, and an image-capturing unit 40 for capturing an image. The blade 30 is connected to the handgrip 20, and the image-capturing unit 40 is movably secured on the blade 30. In use, users may adjust the view of the laryngoscope 10 by pushing or pulling the image-capturing unit 40.

In addition, to enable users to move the image-capturing unit 40 more conveniently, the laryngoscope 10 of the present invention may further comprise an adjustment piece 50. The adjustment piece 50 has a pushing part 52 and a supporting part 51, and said pushing part 52 has a front end 52f and a rear end 52r; The supporting part 51 has a fixed end 51s connected to the handgrip 20 and a joint end 51c pivotally mounted to the rear end 52r of the pushing part 52, with said front end 52f of the pushing part 52 being capable of actuating the image-capturing unit 40.

It should be noted that, although the laryngoscope 10 in this embodiment of the present invention may provide the effect of moving the image-capturing unit 40 by the installation of the adjustment piece 50, users may also achieve the moving effect by directly pushing or pulling the image-capturing unit 40 or through other means without the presence of the adjustment piece 50, because the image-capturing unit 40 is installed movably, for example, by a slide track 56 or other means. Moreover, even if the adjustment piece 50 of the present invention is made by a pivotal connection of the pushing part 52 and the supporting part 51, the actuation of the adjustment piece 50 is not limited hereto. For example, the adjustment piece 50 may also be a roller or a button connected to the image-capturing unit 40. By rolling the roller or pressing the button, users may also adjust the image-capturing unit 40 to a desirable position.

To enable users to observe the image captured by the image-capturing unit 40 in a real-time manner, the laryngoscope 10 may further comprise a display 60. The display 60 may be electrically connected to the image-capturing unit 40 by a wired transmission so as to receive and display the image signal from the image-capturing unit 40. Nonetheless, to reduce the volume and the size of the laryngoscope 10, the display 60 may also be installed at places other than the laryngoscope 10.

In addition, to provide a clearer image, the image-capturing unit 40 may further comprise an illumination unit 41. The illumination unit 41 may be installed on the circumference of the image-capturing unit 40, and the illumination unit 41 is preferably an LED light bulb.

Figure 4:
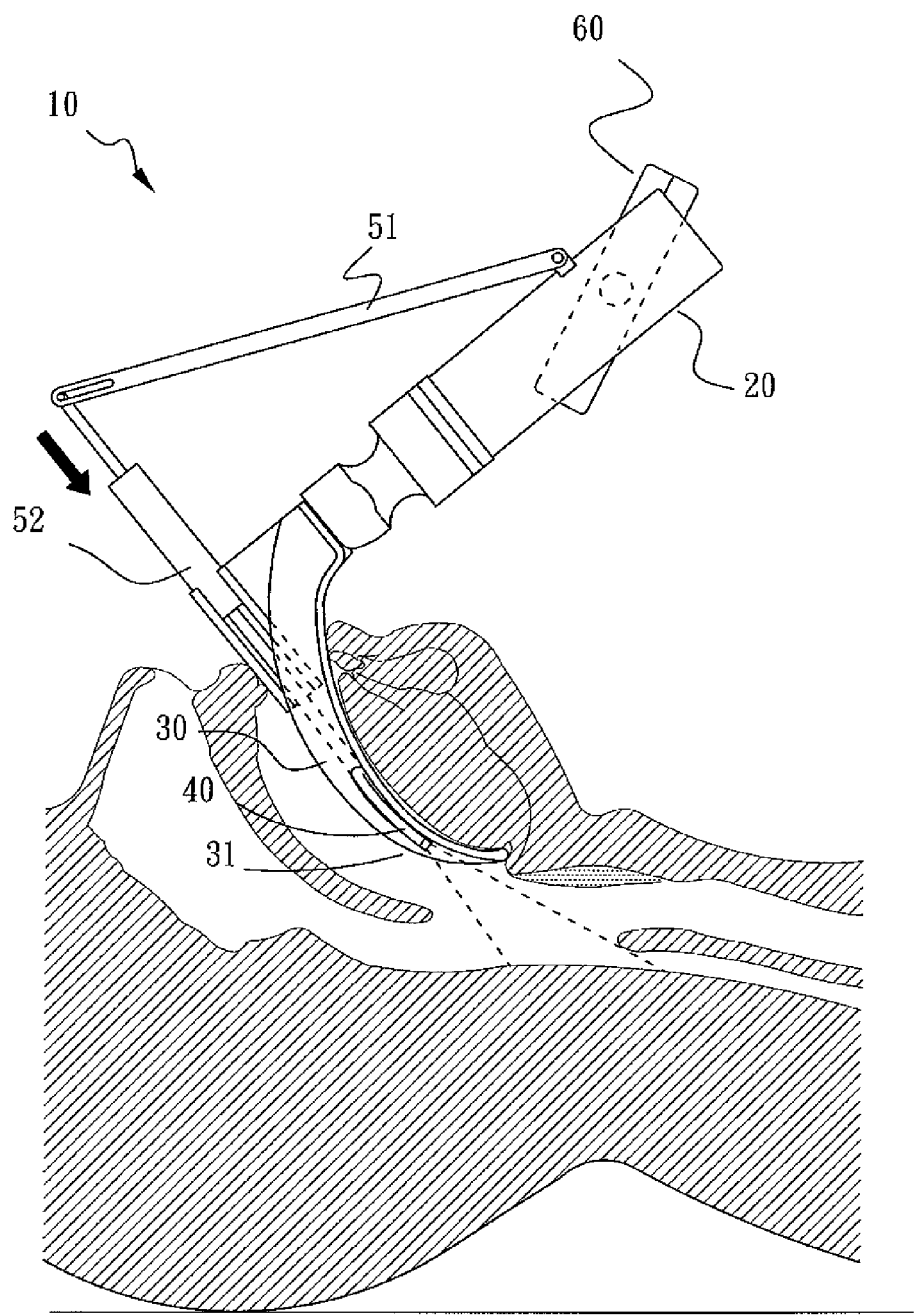
FIG. 4 illustrates the first status in use of a laryngoscope of this invention.

To illustrate the variation of the invention in use, further elaboration is provided hereafter with reference to diagrams. Please turn to FIG. 4 now for an illustration of the first status in use of a laryngoscope 10 of this invention. In use, blade 30 of the laryngoscope 10 of this invention is leaned on the patient's tongue base, and, at the same time, the image-capturing unit 40 of the blade 30 is disposed at a first spot 31.

Figure 5:
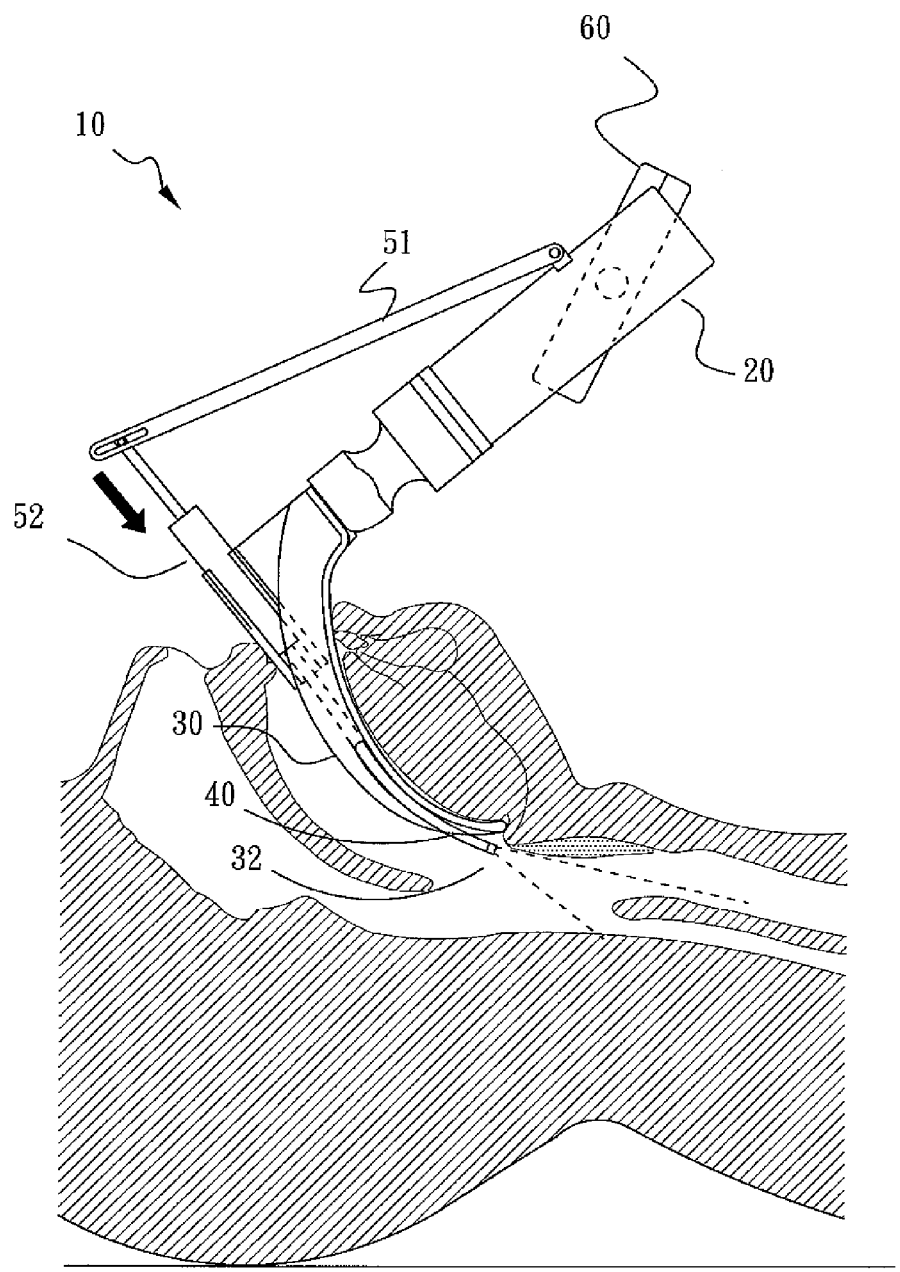
FIG. 5 illustrates the second status in use of a laryngoscope of this invention.

Please refer to FIG. 5 for an illustration of the second status in use of the laryngoscope 10 of this invention. To obtain a better view, users may press the supporting part 51 to push the pushing part 52 connected pivotally thereto. When the pushing part 52 is driven to move, the image-capturing unit 40 is pushed to a second spot 32. By viewing the frame displayed on the display, users may move the image-capturing unit 40 back and forth so as to obtain a better observation angle and view for facilitating the intubation process.

Figure 6:
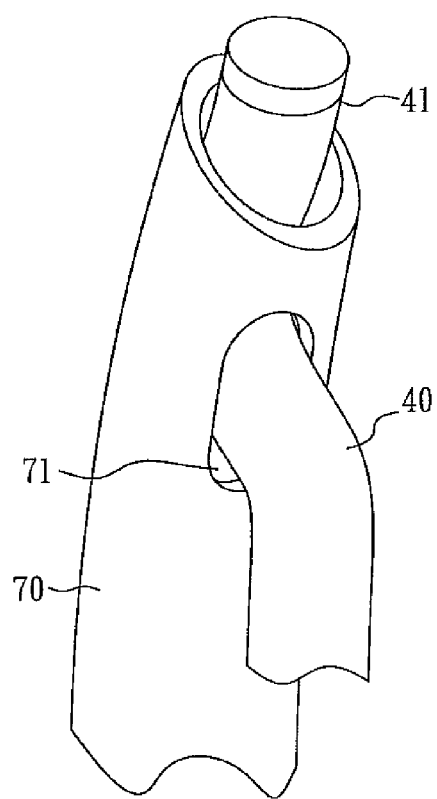
FIG. 6 is an illustrative diagram of the image-capturing unit of the present invention sleeved in the side aperture of an endotracheal tube.
Figure 7:
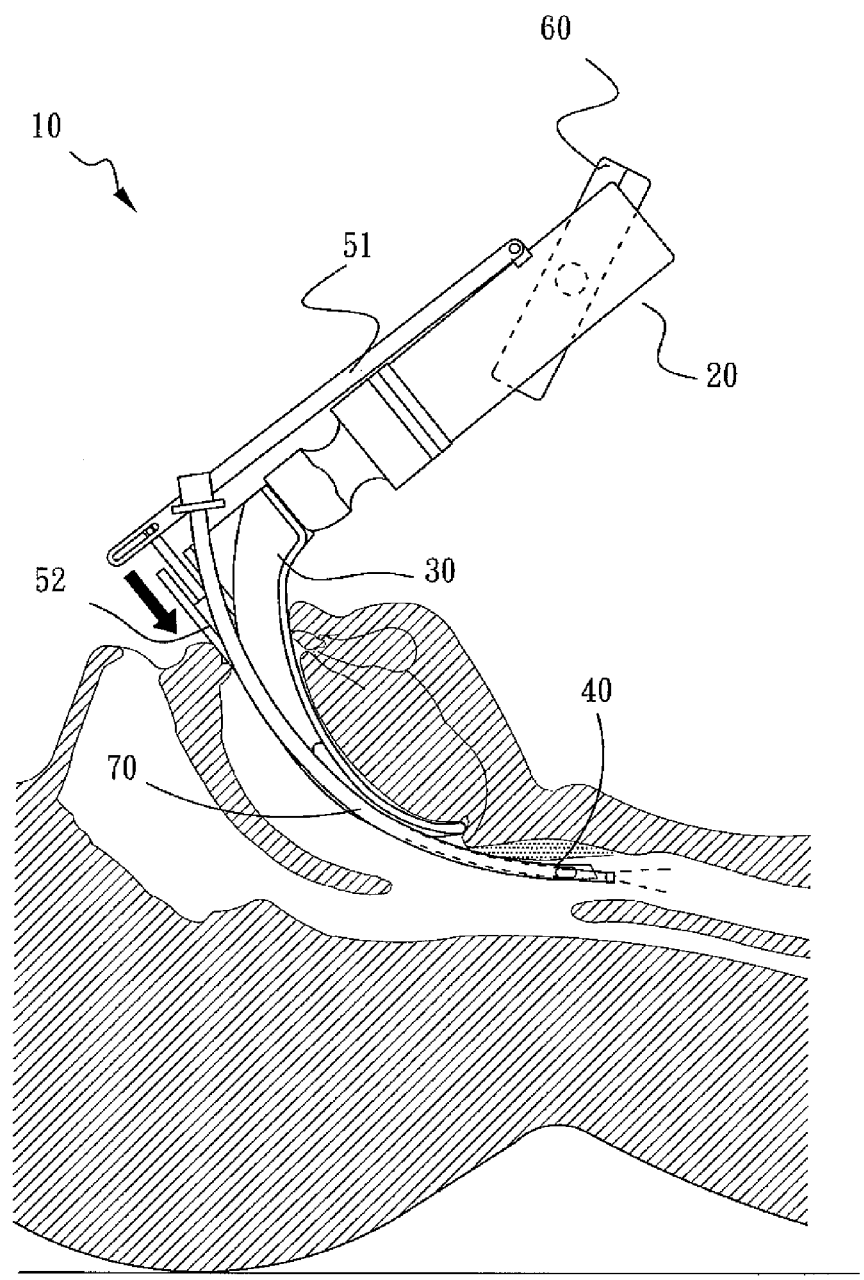
FIG. 7 illustrates the third status in use of a laryngoscope of this invention.

Now refer to FIG. 6 for an illustrative diagram of the image-capturing unit 40 of the present invention sleeved by an endotracheal tube 70. Since the endotracheal tube 70 always has a side aperture 71, namely the Murphy eye, the present invention may increase the efficiency of intubation by combining the image-capturing unit 40 and the endotracheal tube 70. Refer also to FIG. 7 for an illustration of the third status in use of the laryngoscope 10 of this invention. Before using the laryngoscope 10, users may penetrate the image-capturing unit 40 through the side aperture 71 of the endotracheal tube 70 so as to releasably connect the image-capturing unit 40 and the endotracheal tube 70. Then the laryngoscope 10 is moved to a proper place in the patient's upper airway with the endotracheal tube 70. After that, users may move the image-capturing unit 40 to a desirable spot by pressing the supporting part 51. Since the endotracheal tube 70 is sleeved on the image-capturing unit 40, the endotracheal tube 70 will be moved to the same spot as well. At this time, users may push the endotracheal tube 70 over the image-capturing unit 40 so as to deliver the endotracheal tube 70 into the patient's trachea and to release the image capturing unit. The time spent for the intubation may be largely reduced in this embodiment, because the endotracheal tube 70 is located around the image-capturing unit 40, providing images from the area directly in front of the tube.

Figure 8:
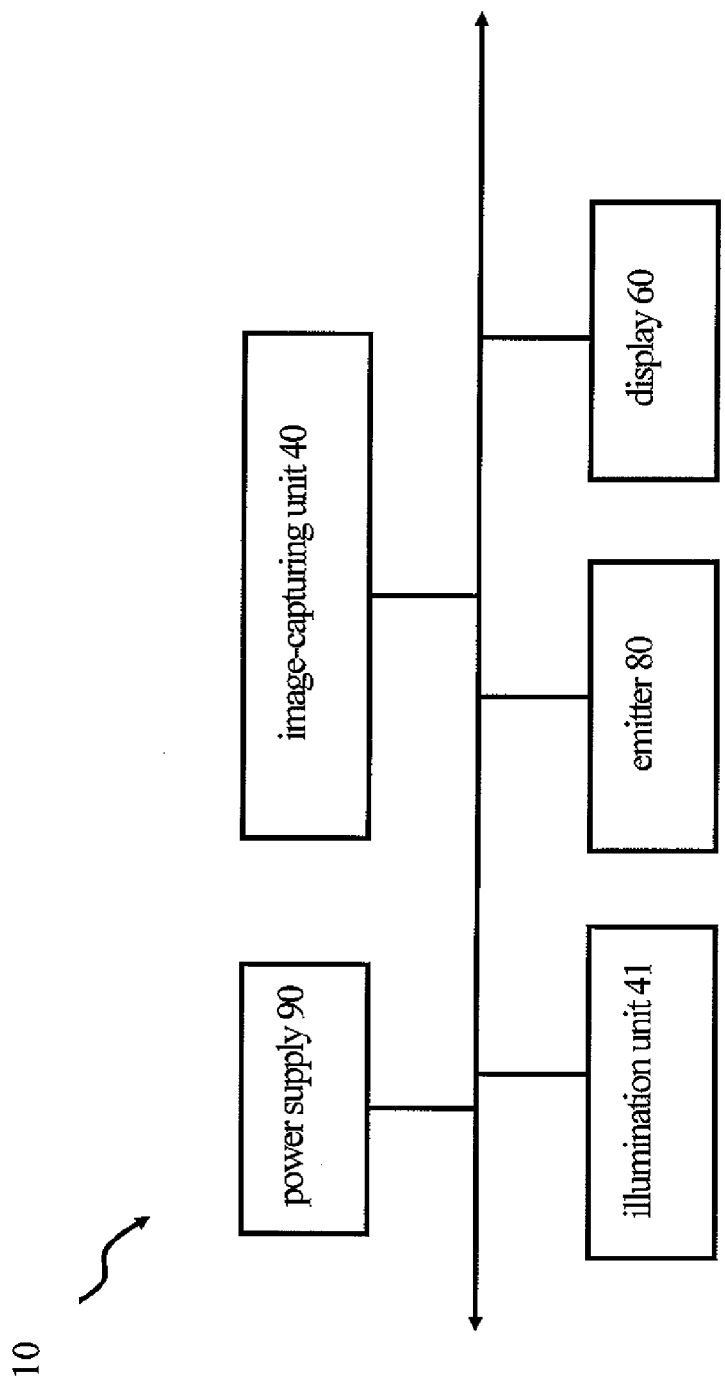
FIG. 8 illustrates the circuit arrangement of a laryngoscope of this invention.

Refer to FIG. 8 for the illustrative diagram showing the circuit arrangement of a laryngoscope 10 of this invention. To reduce the volume and the size of the laryngoscope 10, the display 60 and the laryngoscope 10 may be separated in this invention, and an external display may be adopted by the invention to display the image captured by the image-capturing unit 40. Furthermore, an emitter 80 may be applied to achieve the effect of wireless transmission of the image. Additionally the laryngoscope 10 may further comprise a power supply 90 for providing the electricity demanded by other elements. The power supply 90 is preferably installed in the handgrip 20.

It will be understood that many other modifications can be made to the various disclosed embodiments without departing from the spirit and scope of the invention. For these reasons, the above description should not be construed as limiting the invention, but should be interpreted as merely exemplary of preferred embodiments.

What is claimed is:

1. A laryngoscope comprising:
    a handgrip;
    a blade having a connected end and an opposite end, with the connected end of the blade connected to the handgrip, with the blade having a slide track;
    an image-capturing unit for capturing an image, said image-capturing unit having a free end and being movably installed in the slide track of the blade to adjust positioning of the image-capturing unit in a slide direction along the slide track and relative to the blade in use between a first spot and a second spot, with the free end located at a lesser spacing in the slide direction from the opposite end in the second spot than in the first spot; and
    an adjustment piece driving movement of the image-capturing unit relative to the blade in use, wherein the adjustment piece comprises a pushing part and a supporting part, said pushing part having a front end and a rear end, with the pushing part being slideably mounted on the blade, said supporting part having a fixed end connected to the handgrip and a joint end pivotally mounted to the rear end of the pushing part, said front end of the pushing part pushing and pulling the image-capturing unit between the first and second spots.

2. The laryngoscope as claimed in claim 1, wherein the image captured by the image-capturing unit is transmitted wirelessly.

3. The laryngoscope as claimed in claim 1, further comprising a display for displaying the image, said display being installed on the handgrip.

4. The laryngoscope as claimed in claim 1, wherein the handgrip further comprises a power supply providing electricity to the image-capturing unit.

5. The laryngoscope as claimed in claim 1, wherein the image-capturing unit includes an illumination unit, with the illumination unit moving with movement of the image-capturing device.

6. The laryngoscope as claimed in claim 5, wherein the image captured by the image-capturing unit is transmitted wirelessly.

7. The laryngoscope as claimed in claim 5, further comprising a display for displaying the image, said display being installed on the handgrip.

8. The laryngoscope as claimed in claim 5, wherein the illumination unit is an LED light bulb.

9. The laryngoscope as claimed in claim 1, further comprising an endotracheal tube having a side aperture, with the endotracheal tube extending adjacent to the blade, wherein the image-capturing unit penetrates through the side aperture on the endotracheal tube, with the endotracheal tube sleeved on the image-capturing unit between the free end and the side aperture, with adjusting positioning of the image-capturing unit relative to the blade moving the endotracheal tube relative to the blade.

10. A laryngoscope comprising:
   a handgrip;
   a blade connected to the handgrip;
   an image-capturing unit for capturing an image, said image-capturing unit being movably secured on the blade to adjust positioning of the image-capturing unit relative to the blade in use; and
   an endotracheal tube having a side aperture, with the endotracheal tube extending adjacent to the blade, wherein the image-capturing unit penetrates through the side aperture on the endotracheal tube, with the endotracheal tube sleeved on the image-capturing unit between the free end and the side aperture, with adjusting positioning of the image-capturing unit relative to the blade moving the endotracheal tube relative to the blade.

11. The laryngoscope as claimed in claim 10, further comprising an adjustment piece driving movement of the image-capturing unit relative to the blade in use.

12. The laryngoscope as claimed in claim 11, further comprising a display for displaying the image, said display being installed on the handgrip.

13. The laryngoscope as claimed in claim 12, wherein the adjustment piece comprises a pushing part and a supporting part, said pushing part having a front end and a rear end, with the pushing part being slideably mounted on the blade, said supporting part having a fixed end connected to the handgrip and a joint end pivotally mounted to the rear end of the pushing part, said front end of the pushing part actuating the image-capturing unit.

14. The laryngoscope as claimed in claim 13, wherein the image captured by the image-capturing unit is transmitted wirelessly.

15. The laryngoscope as claimed in claim 13, wherein the handgrip further comprises a power supply providing electricity to the image-capturing unit.

16. The laryngoscope as claimed in claim 13, wherein the image-capturing unit includes an illumination unit, with the illumination unit moving with movement of the image-capturing device.

17. The laryngoscope as claimed in claim 16, wherein the illumination unit is an LED light bulb.

* * * * *